United States Patent [19]
Lubisch et al.

[11] Patent Number: 5,260,330
[45] Date of Patent: Nov. 9, 1993

[54] SUBSTITUTED ANILIDES

[75] Inventors: Wilfried Lubisch, Mannheim; Gerda von Philipsborn, Weinheim; Sabine Schult, Heidelberg; Michael Kirchengast, Speyer, all of Fed. Rep. of Germany

[73] Assignee: BASF Aktiengesellschaft, Ludwigshafen, Fed. Rep. of Germany

[21] Appl. No.: 790,869

[22] Filed: Nov. 12, 1991

[30] Foreign Application Priority Data

Nov. 17, 1990 [DE] Fed. Rep. of Germany ....... 4036782

[51] Int. Cl.$^5$ ................... C07D 202/05; A61K 31/40
[52] U.S. Cl. .................................. 514/428; 548/567; 514/333; 546/221
[58] Field of Search ............... 548/567; 546/221; 514/428, 331

[56] References Cited

U.S. PATENT DOCUMENTS 3,994,900 11/1976 Krapcho et al. .............. 260/286 R

FOREIGN PATENT DOCUMENTS 0352639 1/1990 European Pat. Off. .
1176918 4/1959 France .

OTHER PUBLICATIONS

Circulation 68 (1983) 88, Fogoros et al.
J. American Heart, 109 (1985) 949, Lynch et al.
J. Med. Chem. 12 (1969) 164, Krapcho et al.
Krapcho et al, J. of Medicinal Chemistry, 12 (1), 164–166 (1969).

*Primary Examiner*—David B. Springer
*Attorney, Agent, or Firm*—Keil & Weinkauf

[57] ABSTRACT

Substituted anilides of the formula I

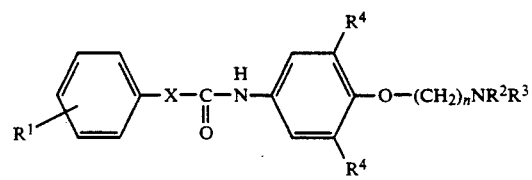

(where
$R^1$ is $C_1$–$C_4$-alkyl, $C_1$–$C_4$-haloalkyl, $C_1$–$C_4$-alkoxy, halogen, cyano, nitro, $C_2$–$C_4$-alkenyl, $C_2$–$C_4$-alkynyl;
X is methylene, ethylene, vinylene;
$R^2$ and $R^3$ are each $C_1$–$C_4$-alkyl, $C_3$–$C_6$-cycloalkyl or together are tetra- or pentamethylene;
$R^4$ is $C_1$–$C_4$-alkyl, methoxy;
n is 2, 3 or 4), and the physiologically tolerated acid addition salts thereof, the pharmaceutical use thereof, drugs produced therefrom and the use thereof for treating cardiac arrhythmias and/or for lowering the heart rate, are described.

12 Claims, No Drawings

SUBSTITUTED ANILIDES

The present invention relates to novel substituted anilides of the formula I

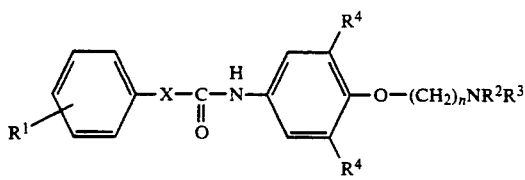

where
$R^1$ is $C_1$-$C_4$-alkyl, $C_1$-$C_4$-haloalkyl, $C_1$-$C_4$-alkoxy, halogen, cyano, nitro, $C_2$-$C_4$-alkenyl, $C_2$-$C_4$-alkynyl;
X is methylene, ethylene, vinylene;
$R^2$ and $R^3$ are each $C_1$-$C_4$-alkyl, $C_3$-$C_6$-cycloalkyl or together are tetra- or pentamethylene;
$R^4$ is $C_1$-$C_4$-alkyl, methoxy;
n is 2, 3 or 4,
and the physiologically tolerated acid addition salts thereof.

The present invention also relates to the pharmaceutical use of the compounds I, to drugs containing the compounds I, and to the preparation of the compounds I and the salts thereof with physiologically tolerated acids for the production of drugs for the treatment of cardiac arrhythmias and/or for reducing the heart rate.

Drugs for the treatment of cardiac arrhythmias (antiarrhythmics) are, according to Vaughan-Williams (see J. Clin. Pharmacol. 24 (1984) 129), divided into 4 classes on the basis of their mode of action:

A. Sodium antagonists
B. Adrenergic β-receptor blockers
C. Calcium antagonists and
D. Repolarization inhibitors.

Class D agents include amiodarone (2-butyl-3-benzofuranyl 4-(2-diethylaminoethoxy)-3,5-diiodophenyl ketone) (see Circulation 68 (1983) 88) and D-sotalol (4'-[1-hydroxy-2-(isopropylamino)ethyl]methanesulfonanilide) (see Am. Heart J. 109 (1985) 949). They differ from antiarrhythmics in the other classes in that they are effective for arrhythmias which are frequently resistant to therapy, such as recurrent ventricular tachycardia and ventricular fibrillation.

J. Med. Chem. 12 (1969) 164 describes cinnamanilides which have immunosuppressant activity and which like compound II

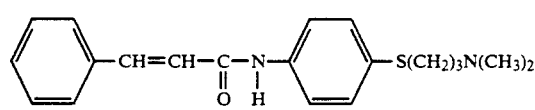

are substituted in position 4' or else position 2' of the anilide residue. They differ from the compounds I defined above in that, inter alia, they are not additionally substituted in positions 3' and 5'.

It is an object of the present invention to provide novel and highly active antiarrhythmics which act as repolarization inhibitors.

We have found that this object is achieved by the compounds I defined above.

We have also found the pharmaceutical use of the compounds I, drugs containing the compounds I, and the use of the compounds I for producing drugs.

Besides their action as antiarrhythmics, the anilides I have also been found to lower the heart rate.

Substituents which are preferred in view of the intended use of the anilides I as antiarrhythmics and agents to lower the heart rate are the following:
$R^1$ $C_1$-$C_4$-alkyl such as methyl, ethyl, propyl, 1-methylethyl, butyl, 1-methylpropyl, 2-methylpropyl and 1,1-dimethylethyl, preferably methyl, ethyl and 1-methylethyl; $C_1$-$C_4$-haloalkyl, preferably $C_1$-$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro- 2-fluoroethyl, 2,2,2-trichloroethyl and pentafluoroethyl, especially difluoromethyl, trifluoromethyl, 2,2,2-trifluoroethyl and pentafluoroethyl; $C_1$-$C_4$-alkoxy such as methoxy, ethoxy, propoxy, 1-methylethoxy, butoxy; halogen such as fluorine and chlorine; cyano; nitro; $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; $C_2$-$C_4$-alkynyl such as ethynyl, 1-propynyl, 2-propynyl, 1-butynyl, 2-butynyl, 3-butynyl, 1-methyl-2-propynyl, especially ethynyl;
X methylene, ethylene, vinylene;
$R^2$, $R^3$ $C_1$-$C_4$-alkyl such as methyl, ethyl, propyl, 1-methylethyl, butyl, 1-methylpropyl, 2-methylpropyl and 1,1-dimethylethyl, preferably methyl, ethyl and 1-methylethyl; $C_3$-$C_6$-cycloalkyl such as cyclopropyl, cyclopentyl and cyclohexyl, or together tetra- or pentamethylene;
$R^4$ $C_1$-$C_4$-alkyl as mentioned for $R^1$, especially methyl, ethyl, propyl, tert-butyl, particularly preferably methyl, tert-butyl; methoxy;
n 2, 3 or 4.

The compounds I are obtained, for example, by initially reacting by known methods (see, inter alia, Houben-Weyl, Volume 6/3, Chapter A II, 1976) the phenol derivative III

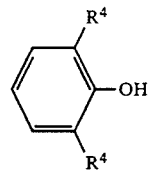

with an amine L-$(CH_2)_n$—$NR^2R^3$ where L is a nucleofugic leaving group such as chlorine, bromine or tosylate, to give the compound IV

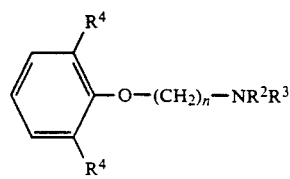

and then nitrating the latter in a conventional manner, for example with nitric acid, in position 4 to give the nitro compound V

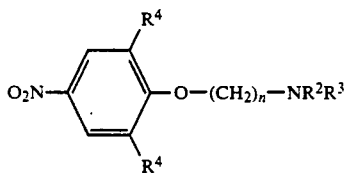

Another method for preparing the compound comprises reacting, in a way similar to the above process, the 4-nitrophenol compound III′

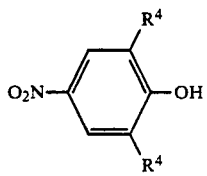

with the amine L—$(CH_2)_n$—$NR^2R^3$. The compounds III′ are known or can be prepared by known methods (see Houben-Weyl, Vol. 10/1; pp. 576 et seq., 1971). The nitro compound V is then reduced in a conventional manner (see Houben-Weyl Vol. XI/1, pp. 341 et seq., 1957) to the aniline compound VI

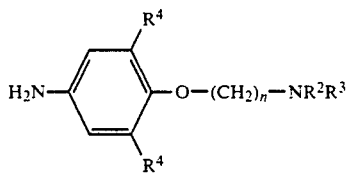

Subsequently the aniline derivative VI is reacted in a conventional manner (see Houben-Weyl, Vol. E5, Chapter V, 1985) with the acid VII

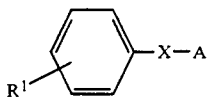

which is in activated form and in which A can be chloroformyl, $C_1$–$C_3$-alkoxycarbonyl such as methoxy-, ethoxy- and propoxycarbonyl, $C_2$–$C_4$-acyloxycarbonyl, especially acetoxycarbonyl, or carbamoyl, to give the anilide I.

Physiologically tolerated acid addition salts can be prepared by reacting the anilides I with conventional acids (see Arzneimittelforschung 10 (1966) 224, Birkhauser Verlag) such as hydrochloric acid, hydrobromic acid, sulfuric acid, phosphoric acid, acetic acid, malonic acid, succinic acid, fumaric acid, maleic acid, citric acid, tartaric acid, lactic acid and oxalic acid in a conventional manner.

The compound I can be administered orally, parenterally or intravenously in free form or, preferably, in the form of a salt with a physiologically tolerated acid (see above).

The dosage depends on the age, condition and weight of the patient and on the mode of administration. As a rule, the daily dose of active substance is from 0.1 to 20, preferably from 1 to 10, mg/kg of body weight on oral use, and from 0.5 to 5, preferably from 1 to 3, mg/kg of body weight on intravenous use.

The compounds I can be used solid or liquid in the conventional pharmaceutical forms, eg. as uncoated or (film-)coated tablets, capsules, pills, powders, solutions or suspensions, infusion or injection solutions, and pastes, ointments, gels, creams, lotions, dusting powders, emulsions and sprays.

The latter are produced in a conventional manner. The active substances can for this purpose be processed with conventional pharmaceutical auxiliaries such as tablet binders, fillers, plasticizers, wetting agents, dispersants, emulsifiers, solvents, retardants and/or antioxidants (cf. H. Sucker et al.: Pharmazeutische Technologie, Thieme Verlag, Stuttgart 1978). The compositions obtained in this way normally contain the active substance in an amount of from 0.1 to 99% by weight.

EXAMPLES

A) Synthetic Examples

Example 1

[3′,5′-Dimethyl-4′-(2-(N-pyrrolidinyl)ethoxy)](2-methylphenyl)acetanilide fumarate 15 ml of 2 molar sodium hydroxide solution were added to 2.3 g (10 mmol) of 3,5-dimethyl-4-(2-(N-pyrrolidinyl)ethoxy)aniline in 100 ml of methylene chloride mixture was then cooled to 0° C, and 3.4 g (20 mmol) of (2-methylphenyl)acetyl chloride were added. After stirring at room temperature for 12 h, the organic phase was separated off and dried over sodium sulfate, after which the solvent was removed under reduced pressure. The crude product was dissolved in i-propanol, and 1.16 g (10 mmol) of fumaric acid were added, whereupon 3.5 g of the acid addition salt crystallized. Melting point 164 to 165° C.

Example 2

[3′,5′-Dimethyl-4′-(2-(N-pyrrolidinyl)ethoxy)]-(2-methylphenyl)acrylanilide fumarate 2.3 g (10 mmol) of 3,5-dimethyl-4-(2-(N-pyrrolidinyl)ethoxy)aniline were reacted with 3.6 g (20 mm o-methylcinnamyl chloride in a similar manner to Example 1. 2.2 g of crystalline product were obtained. Melting point 200° to 203° C.

Example 3

[3′,5′-Dimethyl-4′-(2-(N-pyrrolidinyl)ethoxy)]-3-(2-methylphenyl)propionanilide fumarate 2.2 g of the product from Example 2 were dissolved in 100 ml of methanol and, after addition of 0.25 g of Pd/carbon (10% by weight), hydrogenated at 25° C under a pressure of 1 bar of hydrogen. The reaction mixture was then filtered, and the solvent was removed under reduced pressure. The crude product was converted into the fumarate as in Example 1 and recrystallized from ethanol, resulting in 3.1 g of product. Melting point 174 to 176° C.

B) Pharmacological action

The action of the anilides I as repolarization inhibitors can be demonstrated by ECG measurements. In these the cardiac cycle is divided into systole (contraction of the heart), also called QT interval, and diastole (relaxation of the heart with filling of the ventricles). Repolarization inhibitors increase the QT interval with a negligible effect on the atrioventricular conduction time (PQ interval) and the period of isometric contraction (QRS time, from the start of systole until the semilunar valves open) (see Pschyrembel, 254th edition, 1982).

The activity of the compounds according to the invention as repolarization inhibitors can be investigated in animal experiments by ECG measurements on, for example, guinea pig hearts (see Basic Res. Cardiol. 82 (1987) 437; J. Pharmacol. Methods 21 (1989) 195). Used to compare the activities of a number of substances is, for example, the dose of an agent at which there is a 20% increase in the QT interval from the initial figure ($ED_{20\%}$). This is done by plotting the logarithm of the doses of the particular substances against the experimentally found relative changes in the QT interval, and using linear regression to determine the equation of a straight line from which the $ED_{20\%}$ can be calculated.

This method was used to determine the $ED_{20\%}$ values for the compounds of Examples 2 and 3 (see Table). D-sotalol was used as comparative substance.

The experimental animals were male Duncin-Hartley guinea pigs with a body weight of 300 to 350 g. 30 min after administration of 1250 I.U. of heparin/kg of body weight into the abdominal cavity, the animals were sacrificed by a blow to the back of the neck. After the common carotid arteries had been cut for exsanguination, the thoracic cavity was opened, and the heart was dissected out and attached to a perfusion apparatus. The Langendorff perfusion was carried out with Krebs-Henseleit solution (NaCl 6896 mg/l; KCl 350 mg/l; $MgSO_4$ 285 mg/l; $CaCl_2$ 370 mg/l; $KH_2PO_4$ 161 mg/l; $NaHCO_3$ 2090 mg/l; glucose 2000 mg/l) enriched with oxygen and heated to 37° C. The perfusion volume per unit time was adjusted to 4 to 6 ml/min for a total volume of 100 ml, and the perfusion pressure was adjusted to 60 to 70 mm Hg. Circulating perfusion was carried out after equilibration for 30 min.

The ECG measurements were made via two silver electrodes attached to the surface of the heart in the upper region of the left coronary artery and on the rear of the heart at the level of the valve plane. The PQ and QT intervals, the QRS time and the heart rate were measured.

The substance was administered cumulatively at intervals of 15 min into the perfusate.

TABLE

| Prolongation of the QT interval by compounds 2 and 3 according to the invention compared with D-sotalol | | |
|---|---|---|
| Example No. | $ED_{20\%}$ [μmol/l] | Relative effect $ED_{20\%}$(D-sotalol)/$ED_{20\%}$(Ex.) |
| 2 | 0.50 | 32 |
| 3 | 0.31 | 51 |
| for comparison: D-sotalol | 16.00 | 1 |

We claim:

1. A substituted anilide of the formula I

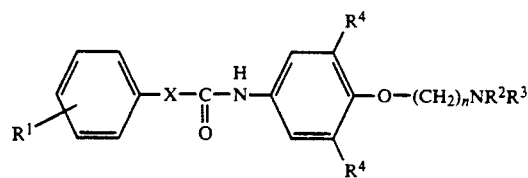

where
$R^1$ is $C_1$-$C_4$-alkyl, $C_1$-$C_4$-haloalkyl, $C_1$-$C_4$-alkoxy, halogen, cyano, nitro, $C_2$-$C_4$-alkenyl, $C_2$-$C_4$-alkynyl;
X is methylene, ethylene, vinylene;
$R^2$ and $R^3$ are taken together and form tetramethylene;
$R^4$ is $C_1$-$C_4$-alkyl, methoxy;
n is 2, 3 or 4, or a physiologically tolerated acid addition salt thereof.

2. A pharmaceutical composition containing an amount of the compound I as defined in claim 1 which is therapeutically effective for cardiac arrhythmias and/or for lowering the heart rate along with at least one pharmaceutical auxiliary.

3. A method for treating cardiac arrhythmias and/or for lowering the heart rate in a patient suffering therefrom, which comprises administering to said patient an effective amount of a compound as defined in claim 1.

4. A substituted anilide of the formula as defined in claim 1, wherein $R^1$ is 2-alkyl or 2-alkoxy, $R^4$ is methyl, X is ethylene or vinylene and n is 2.

5. A substituted anilide as defined in claim 1 which is [3',5'-dimethyl-4'-(2-(N-pyrrolidinyl)ethoxy)]-2-methylphenyl)acetanilide fumarate.

6. A substituted anilide as defined in claim 1 which is [3',5'-dimethyl-4'-(2-(N-pyrrolidinyl)ethoxy)]-2-methylphenyl)acrylanilide fumarate.

7. A substituted anilide as defined in claim 1 which is [3',5'-dimethyl-4'-(2-(N-pyrrolidinyl)ethoxy)]-3-(2-methylphenyl)propionanilide fumarate.

8. A method of treating cardiac arrhythmias and/or for lowering the heart rate in a patient in need thereof, which comprises administering to said patient an effective amount of the compound of claim 5.

9. A method of treating cardiac arrhythmias and/or for lowering the heart rate in a patient in need thereof, which comprises administering to said patient an effective amount of the compound of claim 6.

10. A method of treating cardiac arrhythmias and/or for lowering the heart rate in a patient in need thereof, which comprises administering to said patient an effective amount of the compound of claim 7.

11. A substituted anilide as defined in claim 1, wherein $R^2$ and $R^3$ are taken together and form tetramethylene.

12. A method of treating cardiac arrhythmias and/or lowing the heart rate in a patient in need thereof, which comprises administering to said patient an effective amount of a compound as defined in claim 11.

* * * * *